(12) United States Patent
Van Anholt et al.

(10) Patent No.: US 10,039,732 B2
(45) Date of Patent: Aug. 7, 2018

(54) NUTRITIONAL COMPOSITION FOR IMPROVING BRAIN FUNCTION IN PHENYLKETONURIA

(71) Applicant: N.V. Nutricia, Zoetermeer (NL)

(72) Inventors: Rogier Daniël Van Anholt, Deventer (NL); Amos Attali, Utrecht (NL)

(73) Assignee: N.V. NUTRICIA, Zoetermeer (NL)

( * ) Notice: Subject to any disclaimer, the term of this patent is extended or adjusted under 35 U.S.C. 154(b) by 0 days.

(21) Appl. No.: 14/784,838

(22) PCT Filed: Apr. 17, 2014

(86) PCT No.: PCT/NL2014/050245
§ 371 (c)(1),
(2) Date: Oct. 15, 2015

(87) PCT Pub. No.: WO2014/171828
PCT Pub. Date: Oct. 23, 2014

(65) Prior Publication Data
US 2016/0158177 A1 Jun. 9, 2016

(30) Foreign Application Priority Data

Apr. 17, 2013 (WO) ................ PCT/NL2013/050277

(51) Int. Cl.
| | | |
|---|---|---|
| *A23L 1/30* | (2006.01) | |
| *A61K 38/01* | (2006.01) | |
| *A61K 31/195* | (2006.01) | |
| *A61P 25/00* | (2006.01) | |
| *A61P 25/28* | (2006.01) | |
| *A61K 31/198* | (2006.01) | |
| *A61K 31/202* | (2006.01) | |
| *A61K 31/7068* | (2006.01) | |
| *A61K 31/7072* | (2006.01) | |
| *A61K 31/401* | (2006.01) | |
| *A61K 31/4045* | (2006.01) | |
| *A61K 31/405* | (2006.01) | |
| *A61K 31/4172* | (2006.01) | |
| *A61K 31/70* | (2006.01) | |
| *A61K 38/17* | (2006.01) | |
| *A23L 33/12* | (2016.01) | |
| *A23L 33/13* | (2016.01) | |
| *A23L 33/17* | (2016.01) | |
| *A23L 33/175* | (2016.01) | |

(52) U.S. Cl.
CPC ............ *A61K 31/198* (2013.01); *A23L 33/12* (2016.08); *A23L 33/13* (2016.08); *A23L 33/17* (2016.08); *A23L 33/175* (2016.08); *A61K 31/202* (2013.01); *A61K 31/401* (2013.01); *A61K 31/405* (2013.01); *A61K 31/4045* (2013.01); *A61K 31/4172* (2013.01); *A61K 31/70* (2013.01); *A61K 31/7068* (2013.01); *A61K 31/7072* (2013.01); *A61K 38/01* (2013.01); *A61K 38/1709* (2013.01); *A23V 2002/00* (2013.01); *A23V 2200/00* (2013.01)

(58) Field of Classification Search
None
See application file for complete search history.

(56) References Cited

U.S. PATENT DOCUMENTS

| | | | |
|---|---|---|---|
| 4,252,822 A | 2/1981 | Berry | |
| 2006/0247153 A1 | 11/2006 | McMahon et al. | |
| 2011/0009357 A1* | 1/2011 | Hageman | ................ A23L 33/12 514/51 |

FOREIGN PATENT DOCUMENTS

| | | |
|---|---|---|
| EP | 1 800 675 A1 | 6/2007 |
| EP | 2 162 019 | 3/2010 |
| WO | WO 98/08402 A1 | 3/1998 |
| WO | WO 2006/127620 A2 | 11/2006 |
| WO | WO 2013/129914 A1 | 9/2013 |

OTHER PUBLICATIONS

MacLeod et al., "Nutritional Management of Phenylketonuria," Ann Nestle 68:58-69 (2010).*
Database GNPD [Online] Mintel, Anonymous: "Cooler System", XP002723210, Sep. 2009, retrieved from www.gnpd.com.
Giovannini et al., "Phenylketonuria: nutritional advances and challenges", Nutrition & Metabolism, Feb. 3, 2012, vol. 9, No. 7, pp. 1-7.
Thoma-Worringer et al., "Gewinnung von Caseinomacropeptid durch Membranverfahren und technologischer Einsatz zur Steigerung der ernahrungsphysiologischen Funktionalitat von Milchprodukten", Chemie Ingenieur Technik, Sep. 1, 2006, vol. 78, No. 9, pp. 1231-1232.
Wurtman et al., "Synaptic proteins and phospholipids are increased in gerbil brain by administering uridine plus docosahexaenoic acid orally", Brain Research, Elsevier, May 9, 2006, vol. 1088, No. 1, pp. 83-92.
International Search Report issued in International Patent Application No. PCT/NL2014/050245 dated Jun. 20, 2014.
Liang et al. "Phenylketonuria-related synaptic changes in a BTBR-pah enu2 mouse model", NeuroReport, 2011, vol. 22, No. 2, pp. 617-622.
Thoma-Worringer et al., "Recovery of caseinomacropeptide membrane technology and technological use to increase the nutritional physiological functionality of dairy products", Chemie Ingenieur Technik, Sep. 1, 2006, vol. 78, No. 9, pp. 1231-1232, machine translation.

* cited by examiner

*Primary Examiner* — Julie Ha
*Assistant Examiner* — Kristina M Hellman
(74) *Attorney, Agent, or Firm* — Gilberto M. Villacorta; Sunit Talapatra; Foley & Lardner LLP (57) ABSTRACT

The present invention relates to food compositions comprising nutritional composition for use in the treatment or nutritional management of phenylketonuria or hyperphenylalaninemia or for preserving or improving brain function in PKU or hyperphenylalaninemia. The composition comprises a specific protein source, long chain polyunsaturated fatty acids and at least one of uridine or cytidine.

17 Claims, 1 Drawing Sheet

Fig. 1a

Fig. 1b ated on Jan. 20, 2016, is named Sequence.txt and
NUTRITIONAL COMPOSITION FOR IMPROVING BRAIN FUNCTION IN PHENYLKETONURIA

CROSS-REFERENCE TO RELATED APPLICATIONS

This application is the National Phase of International Patent Application No. PCT/NL2014/050245, filed Apr. 17, 2014, published on Oct. 23, 2014 as WO 2014/171828 A1, which claims priority to International Patent Application No. PCT/NL2013/050277, filed Apr. 17, 2013. The contents of which are herein incorporated by reference in its entirety.

The instant application contains a Sequence Listing which has been submitted in ASCII format via EFS-WEB and is hereby incorporated by reference in its entirety. Said ASII copy, created on Jan. 20, 2016, is named Sequence.txt and is 4 KB.

BACKGROUND OF THE INVENTION

Phenylketonuria (PKU) is the most common inborn aminoacidopathy caused by a deficiency in phenylalanine hydroxylase, resulting in an accumulation of phenylalanine (Phe) and is converted into phenylpyruvate, also known as phenylketone. This accumulation also occurs in the brain.

The genetic mutations characteristic for Phenylketonuria (PKU) impair the proper functioning of the enzyme phenylalanine hydroxylase (PAH), which normally converts phenylalanine (Phe) to tyrosine (Tyr). This mutation causes Phe to accumulate in blood and brain to toxic levels. Additionally, as Tyr is the precursor for the neurotransmitters Dopamine and Noradrenaline, a decrease in Tyr synthesis disrupts the biosynthesis of these catecholamines. In parallel, Phe competes with Tyr and Tryptophan (Trp, the precursor for Serotonin) at amino acid transporters across the blood brain barrier (BBB) and as a consequence, the high Phe concentrations in the blood also leads to a reduced brain entry of Tyr and Trp, further impacting on their availability for neurotransmitter and protein biosynthesis in neurons.

Similarly, mutations in the co-enzyme tetrahydrobiopterin (tetrahydrobiopterin-deficiency) impair proper conversion of Phe to Tyr, resulting in Phe accumulation, or hyperphenylalaninemia. The availability of Dopamine and Serotonin is critical as these neurotransmitters are involved in a variety of functions, particularly in the Prefrontal Cortex which is the main site of higher cognitive functions. In PKU patients still on diet and with plasma Phe concentrations controlled within the recommended levels, metabolism of both Dopamine and Serotonin was proposed to be deficient, as cerebrospinal fluid measurements showed reduced levels of metabolites of these neurotransmitters. In parallel, studies involving early and continuously treated children with PKU have demonstrated deficits in executive functioning, including strategic processing, processing speed, problem solving, non-verbal intelligence, working memory and attention flexibility.

Concluding, PKU disturbs brain development and leads to progressive mental retardation and cognitive defect. Fortunately, some cognitive deficits as well as certain anatomical impairment observed in patients with PKU seem to be reversible. For instance, reaction time, a parameter for processing speed and which has been found reduced in patients with PKU, has shown reversible when off-diet PKU patients return to a protein-free diet supplemented with amino acids. Additionally, white matter deficits and more specifically myelination deficits have been associated with blood Phe levels. Similarly to the effects of re-initiated diet on cognitive functions, it has been observed with Magnetic Resonance Imaging that these myelin deficits may be partially reversed. Lili Liang et al. reported in NeuroReport 2011, 22:617-622 that PKU-related brain impairment is accompanied with abnormalities of dendritic spines and synapses in a BTBR-Pah mouse model.

Outside the field of PKU, EP2162019 discloses a composition comprising a lipid blend optionally in combination with cytidine or uridine for improving brain function in Alzheimer's disease. Synaptic dysfunction in Alzheimer's disease is closely related to beta-Amyloid toxicity, and beta-amyloid plaque deposition as cause for synaptic dysfunction and neurodegeneration. Alzheimer's disease is therefore seen as a loss of existing (functioning) synapses.

The above observations point towards a potential opportunity for an improved dietary intervention aimed at restoring neuronal and cognitive function associated with PKU which is the object of the present invention. Current low-Phe dietary treatment prevents mental retardation, but cognitive outcome remains suboptimal. Therefore a need remains to improve the nutritional treatment of PKU and PKU-related neurological damage as it is presently available in the art, and to improve nutritional treatment of PKU by improving brain functions.

SUMMARY OF THE INVENTION

The inventors realized that in PKU patients the cognitive deficits related to decreased functionality of the brains cells in PKU patients can be improved using a nutritional therapy aiming at reducing phenylalanine levels in the brain in combination with the stimulation of neurotransmitter synthesis and/or release and by stimulating protective and/or supportive processes in brain cells. In contrast to neurodegenerative disorders, increases in phenylalanine in PKU and hyperphenylalaninemia are inherited diseases, that develop from birth resulting in decreased cerebral protein synthesis thereby potentially impairing the formation of synapse in the neuronal network of the brain. The mechanism underlying the neurological problems in Alzheimer's and dementia is therefore very different from the underlying mechanisms in PKU and hyperphenylalaninemia.

A preferred embodiment according to the present invention is a nutritional composition comprising protein, fat and carbohydrate fractions, wherein the protein fraction is essentially free of phenylalanine and comprises free amino acids and/or optionally glyco-macropeptide (GMP), the fat fraction comprises at least one selected from the group consisting of docosahexaenoic acid (22:6; DHA), eicosapentaenoic acid (20:5; EPA) and docosapentaenoic acid (22:5; DPA), or esters thereof, and wherein the composition optionally comprises a carbohydrate fraction comprising between 5-70 en % digestible and optionally between 1-5 en % indigestible carbohydrates based on the total energy content of the composition, and wherein the composition further comprises one or more of uridine and cytidine, or salts, phosphates, acyl derivatives or esters thereof. The invention also pertains to the use of the composition in nutritional management or treatment of hyperphenylalaninemia patients and/or phenylketonuria patients and/or for use in preserving and improving cognitive function and reducing cognitive deficit in phenylketonuria or hyperphenylalaninemia patients.

A preferred embodiment is a nutritional composition for use in the nutritional management or treatment of hyperphenylalaninemia or for use in the nutritional management or treatment of phenylketonuria patients or for improving brain or cognitive function in PKU patients, particularly a nutritional composition for use in the nutritional management of hyperphenylalaninemia or for use in the treatment of phenylketonuria patients or for improving brain or cognitive function in PKU patients, comprising (a) protein fraction, (b) one or more of uridine and cytidine, or salts, phosphates, acyl derivatives or esters thereof; and (c) at least one of docosahexaenoic acid (22:6; DHA), eicosapentaenoic acid (20:5; EPA) and docosapentaenoic acid (22:5; DPA), or esters thereof. Preferably the composition further comprises choline, preferably between 200-600 mg choline per daily dose. It is preferred that the composition comprises at least docosahexaenoic acid (DHA), uridine monophosphate (UMP), and preferably also choline. The protein fraction preferably comprises free amino acids, or the milk protein glycomacropeptide (GMP) or combinations thereof, and is preferably essentially free of phenylalanine. Preferably the composition further comprises a carbohydrate fraction comprising between 5-70 en % digestible and optionally between 1-5 en % indigestible carbohydrates based on the total energy content of the composition. Worded differently, the invention also relates to the use of the above composition in the manufacture of a product for treatment or providing nutritional management of hyperphenylalaninemia patients and/or phenylketonuria patients, particularly for preserving and improving cognitive function and reducing cognitive deficit and/or preserving and improving cognitive function and reducing cognitive deficit associated with phenylketonuria or hyperphenylalaninemia.

Another preferred embodiment according to the invention relates to the use of a composition comprising (a) one or more of uridine and cytidine, or salts, phosphates, acyl derivatives or esters thereof; and (b) at least one of docosahexaenoic acid (22:6; DHA), eicosapentaenoic acid (20:5; EPA) and docosapentaenoic acid (22:5; DPA), or esters thereof, preferably at least UMP and DHA, for use in a supplement in the dietary management of PKU patients in conjunction with a nutritional composition comprising a protein fraction substantially devoid of phenylalanine, wherein the total daily intake of both the supplement and the nutritional composition is between 40-80 g protein, between 25-45 g carbohydrates, and between 0.3 and 4 g of the above-identified omega-3 long chain polyunsaturated fatty acids, preferably between 0.3 and 4 g docosahexaenoic acid (DHA).

The invention also pertains to methods for treatment or providing nutritional management of hyperphenylalaninemia patients and/or phenylketonuria patients, particularly for preserving and improving cognitive function and reducing cognitive deficit and/or preserving and improving cognitive function and reducing cognitive deficit associated with phenylketonuria or hyperphenylalaninemia, said method involving administering said patients the compositions as described throughout the application.

LIST OF PREFERRED EMBODIMENTS

[embodiment 1]. Use of a preparation in the manufacture of a nutritional composition i) for the nutritional management or treatment of hyperphenylalaninemia patients and/or ii) for the nutritional management or treatment of phenylketonuria patients; and/or iii) for preserving and improving cognitive function and reducing cognitive deficit in phenylketonuria or hyperphenylalaninemia patients, preferably a nutritional composition for nutritional management or treatment of hyperphenylalaninemia patients and/or phenylketonuria patients and/or for preserving and improving cognitive function and reducing cognitive deficits in phenylketonuria or hyperphenylalaninemia patients, said nutritional composition comprising;
   a. a protein fraction,
   b. one or more of uridine and cytidine, or salts, phosphates, acyl derivatives or esters thereof; and
   c. at least one of docosahexaenoic acid (22:6; DHA), eicosapentaenoic acid (20:5; EPA) and docosapentaenoic acid (22:5; DPA), or esters thereof.

[embodiment 2]. Use according to embodiment 1, wherein the protein fraction contains less than 0.1 wt % phenylalanine based on total protein content.

[embodiment 3]. Use according to embodiment 1 or 2 wherein the protein fraction comprises at least 50% free amino acids, preferably at least 90% free amino acids, and wherein the protein fraction optionally comprises glycomacropeptide in intact or hydrolysed form.

[embodiment 4].Use according to embodiment 1 or 2 wherein the protein fraction comprises at least 50 wt % glycomacropeptide (GMP) based on the total protein content.

[embodiment 5]. Use according to any of the preceding embodiments, wherein the composition further comprises choline, preferably between 200-600 mg choline per daily dose.

[embodiment 6]. Use according to any of the preceding embodiments, wherein the composition is a liquid composition further comprising a combination of pectin and at least one indigestible carbohydrate selected from the group of xanthan gum and/or guar gum.

[embodiment 7]. Use according to embodiment 6, wherein the viscosity of the composition is between 5 and 1500 mPa·s, at 20 degrees Celsius at a shear rate of 100/s.

[embodiment 8]. A nutritional composition comprising a protein fraction, a fat fraction and a carbohydrate fraction, wherein the protein fraction is essentially free of phenylalanine and comprises free amino acids and optionally glycomacropeptide, the fat fraction comprises at least one of docosahexaenoic acid (22:6; DHA), eicosapentaenoic acid (20:5; EPA) and docosapentaenoic acid (22:5; DPA), or esters thereof, and wherein the composition optionally comprises a carbohydrate fraction comprising between 5-70 en % digestible and optionally between 1-5 en % indigestible carbohydrates based on the total energy content of the composition, and wherein the composition further comprises one or more of uridine and cytidine, or salts, phosphates, acyl derivatives or esters thereof.

[embodiment 9]. The nutritional composition according to embodiment 8 comprising between 30-65 en % protein, and between 1 and 15 en % fat, and between 1 and 60 en % digestible carbohydrates, and wherein the composition is a liquid with a total caloric density between 50 and 300 kcal/100 ml.

[embodiment 10]. Use of the nutritional composition according to embodiment 8 or 9 for the dietary management of PKU or hyperphenylananinemia.

[embodiment 11]. Use of the composition according to embodiment 8 or 9 in the manufacture of a product for preserving and improving cognitive function and reducing cognitive deficits associated with phenylketonuria or hyperphenylalaninemia.

[embodiment 12]. Use of a composition comprising (a) uridine and cytidine, or salts, phosphates, acyl derivatives or esters thereof; and (b) docosahexaenoic acid (22:6; DHA), in the manufacture of a supplement in the dietary management of PKU or hyperphenylananinemia, wherein said supplement is administered in conjunction with a nutritional composition comprising a protein source substantially devoid of phenylalanine, wherein the total daily intake of both the supplement and the nutritional composition is between 40-80 g protein, between 25-45 g carbohydrates, and between 0.3 and 4 g docosahexaenoic acid (DHA).

[embodiment 13]. A nutritional composition for use in i) the nutritional management or treatment of hyperphenylalaninemia patients and/or ii) the nutritional management or treatment of phenylketonuria patients; and/or iii) preserving and improving cognitive function and reducing cognitive deficit in phenylketonuria or hyperphenylalaninemia patients, particularly for use in nutritional management or treatment of hyperphenylalaninemia patients and/or phenylketonuria patients and/or for use in preserving and improving cognitive function and reducing cognitive deficit in phenylketonuria or hyperphenylalaninemia patients, said nutritional composition comprising:
 a. a protein fraction,
 b. one or more of uridine and cytidine, or salts, phosphates, acyl derivatives or esters thereof; and
 c. at least one of docosahexaenoic acid (22:6; DHA), eicosapentaenoic acid (20:5; EPA) and docosapentaenoic acid (22:5; DPA), or esters thereof,
wherein the protein fraction is essentially free of phenylalanine and comprises free amino acids and optionally glycomacropeptide, and wherein the composition optionally comprises a carbohydrate fraction comprising between 5-70 en % digestible carbohydrates.

[embodiment 14]. A composition comprising (a) uridine and cytidine, or salts, phosphates, acyl derivatives or esters thereof; and (b) docosahexaenoic acid (22:6; DHA), for use in a supplement in the dietary management of PKU or hyperphenylananinemia, wherein said supplement is administered in conjunction with a nutritional composition comprising a protein source substantially devoid of phenylalanine, wherein the total daily intake of both the supplement and the nutritional composition is between 40-80 g protein, between 25-45 g carbohydrates, and between 0.3 and 4 g docosahexaenoic acid (DHA).

[embodiment 15]. A method for treatment or providing nutritional management of hyperphenylalaninemia patients and/or phenylketonuria patients, particularly for preserving and improving cognitive function and reducing cognitive deficit and/or preserving and improving cognitive function and reducing cognitive deficit associated with phenylketonuria or hyperphenylalaninemia, said method involving administering said patients a composition comprising:
 a. a protein fraction,
 b. one or more of uridine and cytidine, or salts, phosphates, acyl derivatives or esters thereof; and
 c. at least one of docosahexaenoic acid (22:6; DHA), eicosapentaenoic acid (20:5; EPA) and docosapentaenoic acid (22:5; DPA), or esters thereof,
wherein the protein fraction is essentially free of phenylalanine and comprises free amino acids and optionally glycomacropeptide, and wherein the composition optionally comprises a carbohydrate fraction comprising between 5-70 en % digestible carbohydrates.

[embodiment 16]. A method for treatment or providing i) nutritional management or treatment of hyperphenylalaninemia patients and/or ii) nutritional management or treatment of phenylketonuria patients; and/or iii) preserving and improving cognitive function and reducing cognitive deficit in phenylketonuria or hyperphenylalaninemia patients, preferably a method for treating or providing nutritional management of hyperphenylalaninemia patients and/or phenylketonuria patients, particularly for preserving and improving cognitive function and reducing cognitive deficit and/or preserving and improving cognitive function and reducing cognitive deficit associated with phenylketonuria or hyperphenylalaninemia,
said method involving administering said patients a composition comprising (a) uridine and cytidine, or salts, phosphates, acyl derivatives or esters thereof; and (b) docosahexaenoic acid (22:6; DHA), wherein said supplement is administered in conjunction with a nutritional composition comprising a protein source substantially devoid of phenylalanine, wherein the total daily intake of both the supplement and the nutritional composition is between 40-80 g protein, between 25-45 g carbohydrates, and between 0.3 and 4 g docosahexaenoic acid (DHA).

DETAILED DESCRIPTION OF THE INVENTION

Protein

The protein in the product according to the invention, either for use as a supplement or a balanced nutritional composition, should be low in phenylalanine. Because PKU is a chronic disease it is important that the product is well palatable. The protein fraction is understood to comprise mainly free amino acids, and/or a non-allergenic protein source such as GMP. According to the present invention, free amino acids are amino acids not coupled to other amino acids, but it still includes amino acids salts or di- and tripeptides such as cystine or gly-gly dipeptides. An absolute phenylalanine free product can be obtained when using free amino acids, and the composition of the amino acids can be easily adapted to the nutritional requirements depending on the age of the patients. Such proteinaceous compositions tailored to PKU patients are available in the art.

Disadvantage of most free amino acid compositions is that palatability is poor, particularly due to organoleptically poor amino acids Met, Cys, Lys and Trp. Replacing part of the free amino acids by an intact protein glycomacro peptide (GMP), which is a protein originating from casein and is low in phenylalanine, can improve the taste significantly, without significantly increasing the phenylalanine content of the formula. Therefore, a preferred embodiment according to the present invention comprises a mixture of GMP supplemented with free amino acids. Preferably the composition comprises at least 50 wt % GMP based on the total protein content. Even more preferably the composition according to the present invention comprises between 50 and 95 wt % GMP, even more preferably between 70 and 90 wt % GMP, supplemented to 100% with free amino acids. GMP is a casein-derived whey peptide. When milk is treated with chymosin during cheese making, the milk protein (k-casein) is hydrolyzed into two peptides. The GMP protein can e.g. be bought from Davisco.

With the terms 'substantially devoid from Phe' or 'essentially free of phenylalanine' used throughout the application it is understood that the proteinaceous material according to the invention preferably contains less than 1.0 wt % phenylalanine, more preferably less than 0.5 wt % Phe, more preferably less than 0.2 wt % Phe, even more preferably less than 0.1 wt % Phe, based on the total proteinaceous content of the composition. In one embodiment, there is no Phe present as free amino acid.

A preferred amino acid composition according to the present invention has a relatively high content of branched chain amino acids (BCAA) leucine, isoleucine and valine. These amino acids can potentially block the transport of phenylalanine over the intestinal barrier and also over the blood-brain barrier thereby helping in lowering the levels of phenylalanine in the brain. Preferably the protein fraction comprises at least 15 wt % BCAA, more preferably between 15 and 35 wt %, even more preferably between 18 and 26 wt % based on the total protein content.

In one embodiment, the composition is used as a complete nutritional product, replacing at least all other protein sources in the diet of the PKU patient; it is preferred that all essential amino acids are present in the product. Essential amino acids are amino acids that cannot be synthesized de novo by humans, and therefore must be supplied in the diet. Essential amino acids are the three BCAAs identified above and histidine, methionine, lysine, threonine and tryptophan (phenylalanine is also a BCAA but—as explained above—but its amounts should be kept as low as possible). A preferred embodiment according to the present invention therefore comprises the BCAA leucine, isoleucine and valine, histidine, methionine, lysine, threonine and tryptophan. Preferably at least 50 wt % of the protein fraction comprises leucine, isoleucine, valine, histidine, methionine, lysine, threonine and tryptophan, more preferably at least 55%, 60%, 65%, 70% of weight of the protein fraction comprises these essential amino acids, as the sum of these amino acids either in free form or part of a non-allergic protein source such as GMP. It is preferred that between 50 and 100 wt %, more preferably between 70 and 100% of the protein fraction comprises leucine, isoleucine, valine, histidine, methionine, lysine, threonine and tryptophan.

DHA/EPA/DPA

The composition comprises at least one ω-3 polyunsaturated fatty acid (LC PUFA; having a chain length of 18 and more carbon atoms) selected from the group consisting of docosahexaenoic acid (22:6; DHA), eicosapentaenoic acid (20:5; EPA) and docosapentaenoic acid (22:5 ω-3; DPA), preferably at least one of DHA and EPA. Preferably the present composition contains at least DHA, more preferably DHA and EPA. EPA is converted to DPA (ω-3), increasing subsequent conversion of DPA to DHA in the brain. Hence, the present composition preferably contains a significant amount of EPA, so to further stimulate in vivo DHA formation.

The DHA, EPA and/or DPA are preferably provided as triglycerides, diglycerides, monoglycerides, free fatty acids or their salts or esters, phospholipids, lysophospholipids, glycerol ethers, lipoproteins, ceramides, glycolipids or combinations thereof. Preferably, the present composition comprises at least DHA in triglyceride form.

In terms of daily dosage, the present method preferably comprises the administration of 400 to 5000 mg DHA+EPA+DPA (preferably DHA+EPA) per day, more preferably 500 to 3000 mg (preferably DHA+EPA) per day, most preferably 1000 to 2500 mg (preferably DHA+EPA) per day. DHA is preferably administered in an amount of 300 to 4000 mg per day, more preferably 500 to 2500 mg per day.

The present composition preferably comprises 1-40 wt. % DHA based on total fatty acids, preferably 3-36 wt. % DHA based on total fatty acids, more preferably 10-30 wt. % DHA based on total fatty acids. The present composition preferably comprises 0.5-20 wt. % EPA based on total fatty acids, preferably 2-10 wt. % EPA based on total fatty acids, more preferably 5-10 wt. % EPA based on total fatty acids. The above-mentioned amounts take into account and optimize several aspects, including taste (e.g. too high LCP levels reduce taste, resulting in a reduced compliance).

The present composition preferably contains at least one oil selected from fish oil, algae oil and eggs lipids. Preferably the present composition contains fish oil comprising DHA and EPA.

The ratio of the weights of DHA to EPA is preferably larger than 1, more preferably 2:1 to 10:1, more preferably 3:1 to 8:1. The above-mentioned ratios and amounts take into account and optimize several aspects, including taste (too high LCP levels reduce taste, resulting in a reduced compliance), balance between DHA and precursors thereof to ensure optimal effectiveness while maintaining low-volume formulations. Sources of DHA possible sources of DHA: tuna oil, (other) fish oils, DHA rich alkyl esters, algae oil, egg yolk, or phospholipids enriched with n-3 LCPUFA e.g. phosphatidylserine-DHA.

The present composition preferably contains a very low amount of arachidonic acid (AA). Preferably the weight ratio DHA/AA in the present composition is at least 5, preferably at least 10, more preferably at least 15, preferably up to e.g. 30 or even up to 60. The present method preferably comprises the administration of a composition comprising less than 5 wt. % arachidonic acid based on total fatty acids, more preferably below 2.5 wt. %, e.g. down to 0.5 wt %.

Uridine, UMP

The composition according to the invention comprises one of more of uridine, cytidine and/or an equivalent thereof, including salts, phosphates, acyl derivatives and/or esters. The composition preferably comprises at least one uridine or an equivalent thereof selected from the group consisting of uridine (i.e. ribosyl uracil), deoxyuridine (deoxyribosyl uracil), uridine phosphates (UMP, dUMP, UDP, UTP), nucleobase uracil and acylated uridine derivatives. In one embodiment, cytidine, CMP, citicoline (CDP-choline) may also be applied. Preferably, the composition to be administered according to the present invention comprises a source of uridine selected from the group consisting of uridine, deoxyuridine, uridine phosphates, uracil, and acylated uridine. Preferably, the composition according to the invention comprises an uridine phosphate selected from the group consisting of uridine monophosphate (UMP), uridine diphosphate (UDP) and uridine triphosphate (UTP); and/or a cytidine phosphate (CMP, CDP, CTP, preferably CMP). In a preferred embodiment, the composition comprises at least one of the aforementioned uridine phosphates. Most preferably the present composition comprises UMP, as UMP is most efficiently being taken up by the body.

Preferably at least 50 weight % of the uridine in the present composition is provided by UMP, more preferably at least 75 weight %, most preferably at least 95 weight %. Doses administered are given as UMP. The amount of uracil sources can be calculated taking the molar equivalent to the UMP amount (molecular weight 324 Dalton).

The present method preferably comprises the administration of uridine (the cumulative amount of uridine, deoxyuridine, uridine phosphates, nucleobase uracil and acylated uridine derivatives) in an amount of in an amount of 0.08-3 g per day, preferably 0.1-2 g per day, more preferably 0.2-1 g per day. The present method preferably comprises the administration of a composition comprising uridine in an amount of 0.08-3 g UMP per 100 ml liquid product, preferably 0.1-2 g UMP per 100 ml liquid product, more preferably 0.2-1 g UMP per 100 ml liquid product. Preferably 1-37.5 mg UMP per kilogram body weight is administered per day, more preferably 5-35, even more preferably 5-30 mg UMP/kg body weight. The above amounts also account for any amounts of cytidine, cytidine phosphates and citicoline incorporated in the composition or method. Preferably, the present composition comprises uridine phosphate, preferably uridine monophosphate (UMP). The UMP is very efficiently taken up by the body. Hence, inclusion of UMP in the present composition enables a high effectivity or efficacy at the lowest dosage and/or the administration of a low volume to the subject.

Choline

In a preferred embodiment, the composition according to the present invention contains choline, a choline salt and/or choline ester. For the remainder of the paragraph, the term 'choline' shall be considered to encompass all these equivalents. The choline salt is preferably selected from choline chloride, choline bitartrate, or choline stearate. The choline ester is preferably selected from a phosphatidylcholine and lyso-phosphatidylcholine. The present method preferably comprises the administration of more than 50 mg choline per day, preferably 80 to 2000 mg choline per day, more preferably 120 to 1000 mg choline per day, most preferably 200 to 600 mg choline per day. The present composition preferably comprises 50 mg to 3000 gram choline per 100 ml of the liquid composition, preferably 200 mg to 1000 mg choline per 100 ml. The above numbers are based on choline, the amounts of choline equivalents or sources can be calculated taking the molar equivalent to choline into account, based on the molar mass of 104 g choline/mol.

Phospholipids

Preferably, the composition according to the present invention comprises phospholipids, preferably 0.1-50 wt. % phospholipids based on total weight of lipids, more preferably 0.5-20 wt. %, more preferably between 1 and 10% wt. %, most preferably between 1 and 5 wt. % based on total weight of lipids. The total amount of lipids is preferably between 10 and 30 wt. % on dry matter, and/or between 2 and 10 g lipid per 100 ml for a liquid composition. The composition preferably comprises between 0.01 and 1 gram lecithin per 100 ml, more preferably between 0.05 and 0.5 gram lecithin per 100 ml. A composition with these preferred amounts was found to be very effective. In one embodiment, the phospholipids comprise at least two phospholipids selected from the group consisting of phosphatidylcholine, phosphatidylethanolamine, phosphatidylinositol and phosphatidylserine, preferably at least PC and PE.

Vitamins

The composition according to the present invention preferably comprises at least one B complex vitamin. The vitamin B is selected from the group of vitamin B1 (thiamine), vitamin B2 (riboflavin), vitamin B3 (niacin or niacinamide), vitamin B5 (panthotenic acid), vitamin B6 (pyridoxine, pyridoxal, or pyridoxamine, or pyridoxine hydrochloride), vitamin B7 (biotin), vitamin B9 (folic acid or folate), and vitamin B12 (various cobalamins). Functional equivalents are encompassed within these terms.

Preferably, at least one vitamin B is selected from the group of vitamin B6, vitamin B12 and vitamin B9. Preferably the composition comprises at least two selected from the group consisting of vitamin B6, vitamin B12 and vitamin B9. In particular, good results have been achieved with a combination comprising vitamin B6, vitamin B12 and vitamin B9. Again, functional equivalents are encompassed within these terms.

The vitamin B is to be administered in an effective dose, which dose depends on the type of vitamin B used. As a rule of thumb, a suitable minimum or a maximum dose may be chosen based on known dietary recommendations, for instance as recommended by Institute of Medicine (TOM) of the U.S. National Academy of Sciences or by Scientific Committee on Food (a scientific committee of the EU), the information disclosed herein and optionally a limited amount of routine testing. A minimum dose may be based on the estimated average requirement (EAR), although a lower dose may already be effective. A maximum dose preferably does not exceed the tolerable upper intake levels (UL), as recommended by IOM.

If present in the nutritional composition or medicament, the vitamin B6 is preferably present in an amount to provide a daily dosage in the range of 0.1 to 100 mg, in particular in the range of 0.5 to 25 mg, more in particular in the range of 0.5 to 5 mg. The present composition preferably comprises 0.1 to 100 mg vitamin B6 per 100 g (liquid) product, more preferably 0.5 to 5 mg vitamin B6 per 100 g (liquid) product, more preferably 0.5 to 5 mg vitamin B6 per 100 g (liquid) product.

If present in the nutritional composition or medicament, the vitamin B12 is preferably present in an amount to provide a daily dosage in the range of 0.5 to 15 µg, in particular in the range of 1 to 10 µg, more in particular in the range of 1.5 to 5 µg. The present composition preferably comprises 0.5-15 µg vitamin B12 per 100 g (liquid) product, more preferably 1 to 10 µg vitamin B12 per 100 g (liquid) product, more preferably 1.5 to 5 µg vitamin B12 per 100 g (liquid) product. The term "vitamin B12" incorporates all cobalamin equivalents known in the art.

Throughout the application, the terms 'folic acid', 'folate' and 'B9' are used interchangeably. If present in the nutritional composition or medicament, the vitamin B9 is preferably present in an amount to provide a daily dosage in the range of 50 to 1000 µg, in particular in the range of 150 to 750 µg, more in particular in the range of 200 to 500 µg. The present composition preferably comprises 50 to 1000 µg folic acid per 100 g (liquid) product, more preferably 150 to 750 µg folic acid per 100 g (liquid) product, more preferably 200 to 500 µg folic acid per 100 g (liquid) product. Folates include folic acid, folinic acid, methylated, methenylated and formylated forms of folates, their salts or esters, as well as their derivatives with one or more glutamic acid, and all in either reduced or oxidized form.

Vitamins C, E

Vitamin C, or a functional equivalent thereof, may be present in an amount to provide a daily dosage in the range of 20 to 2000 mg, in particular in the range of 30 to 500 mg, more in particular in the range of 75 to 150 mg. In one embodiment, vitamin C, or a functional equivalent thereof, is present in an amount in the range of 20 to 2000 mg, in particular in the range of 30 to 500 mg, more in particular in the range of 75 to 150 mg per 100 ml of the composition.

Tocopherol and/or an equivalent thereof (i.e. a compound having vitamin E activity) may be present in an amount to provide a daily dosage in the range of 10 to 300 mg, in particular in the range of 30 to 200 mg, more in particular in the range of 35 to 100 mg, to prevent oxidative damage resulting from dietary PUFA. In one embodiment, tocopherol and/or equivalent is present in an amount in the range of 10 to 300 mg, in particular in the range of 30 to 200 mg, more in particular in the range of 35 to 100 mg per 100 ml of the composition. The term "tocopherol and/or an equivalent thereof", and 'alpha-TE', as used in this description, comprises tocopherols, tocotrienols, pharmaceutical and/or nutritional acceptable derivatives thereof and any combination thereof. The above numbers correspond to the amount of alpha-tocopherol, recognized in the art.

Selenium

The present composition preferably contains selenium, because of its antioxidant activity. Preferably the present method provides the administration of a composition comprising 0.01 and 5 mg selenium per 100 ml liquid product, preferably 0.02 and 0.1 mg selenium per 100 ml liquid product. The amount of selenium administered per day is preferably more than 0.01 mg, more preferably 0.01 to 0.5 mg.

In a preferred embodiment, the composition further comprises, per daily dose or preferably per 100 ml composition: 200-600 mg choline, 50-1000 mg phospholipids, 0.5-3 mg vitamin B6, 50-500 µg folic acid, and 1-30 µg vitamin B12.

More preferably, the composition comprises, per daily dose or preferably per 100 ml composition:
100-500 mg, preferably 200-400 mg EPA,
1000-1500 mg, preferably 1100-1300 mg DHA,
50-600 mg, preferably 60-200 mg phospholipids,
200-600 mg, preferably 300-500 mg choline,
400-800 mg, preferably 500-700 mg UMP (uridine monophosphate),
20-60 mg, preferably 30-50 mg vitamin E (alpha-TE),
60-100 mg, preferably 70-90 mg vitamin C,
40-80 µg preferably 50-70 µg selenium,
1-5 µg preferably 2-4 µg vitamin B12,
0.5-3 mg, preferably 0.5-2 mg vitamin B6, and
200-600 µg, preferably 300-500 µg folic acid.

In one aspect of the invention, the compositions either as complete nutrition or as a supplement as detailed above are intended for use in the nutritional management of hyperphenylalaninemia patients, for use in the treatment of phenylketonuria patients or for improving brain or cognitive function in these patients, particularly PKU patients.

The term 'improving brain or cognitive function' includes preventing or minimizing the risk of brain or cognitive deficits, slowing mental retardation and decreasing the risk of seizures and tremors and improving attention deficits (i.e. concentration problems).

The invention is particularly directed to preserving and improving cognitive function and reducing cognitive deficit which is associated with phe accumulation, particularly humans identified as PKU patients.

In one aspect, the invention pertains to a method for treatment or providing i) nutritional management or treatment of hyperphenylalaninemia patients and/or ii) nutritional management or treatment of phenylketonuria patients; and/or iii) preserving and improving cognitive function and reducing cognitive deficit in phenylketonuria or hyperphenylalaninemia patients, preferably a method for treating or providing nutritional management of hyperphenylalaninemia patients and/or phenylketonuria patients, particularly for preserving and improving cognitive function and reducing cognitive deficit and/or preserving and improving cognitive function and reducing cognitive deficit associated with phenylketonuria or hyperphenylalaninemia, said method involving administering said patients the compositions as defined here above.

In another aspect, the invention pertains to the above compositions (as a complete nutrition or a supplement) for use in i) nutritional management or treatment of hyperphenylalaninemia patients and/or ii) nutritional management or treatment of phenylketonuria patients; and/or iii) preserving and improving cognitive function and reducing cognitive deficit in phenylketonuria or hyperphenylalaninemia patients, preferably a composition for use in the treatment or nutritional management of hyperphenylalaninemia patients and/or phenylketonuria patients, particularly for use in preserving and improving cognitive function and reducing cognitive deficit in phenylketonuria or hyperphenylalaninemia patients and/or preserving and improving cognitive function and reducing cognitive deficit associated with phenylketonuria or hyperphenylalaninemia.

In another aspect, the invention pertains to the use of a compositions as defined here above in the manufacture of a product (as a complete nutrition or a supplement) for i) nutritional management or treatment of hyperphenylalaninemia patients and/or ii) nutritional management or treatment of phenylketonuria patients; and/or iii) preserving and improving cognitive function and reducing cognitive deficit in phenylketonuria or hyperphenylalaninemia patients, preferably a product for treatment or nutritional management of hyperphenylalaninemia patients and/or phenylketonuria patients, particularly for preserving and improving cognitive function and reducing cognitive deficit in phenylketonuria or hyperphenylalaninemia patients and/or preserving and improving cognitive function and reducing cognitive deficit associated with phenylketonuria or hyperphenylalaninemia.

EXAMPLES

In the examples below, patients with PKU will consume Phe-free amino acid supplements to compensate for the reduction of natural sources of protein that is needed to prevent excess Phe intake. These supplements are enriched with vitamins, minerals, trace elements, and/or long chain polyunsaturated fatty acids to balance the changes induced by the restrictive, low protein, diet that the patient is adhering to. When for example an adult patient is required to take 60 g Protein Equivalent (PE) per day, this can be divided into 3 equal servings of 20 g PE, to be taken throughout the day.

Example 1

4 servings per day; 3 standard supplements+1 serving of a supplement according to the invention.

Daily nutritional requirements are provided by 3 servings of a standard amino acids- and micronutrients-containing supplement+1 serving containing the daily amounts of nutrients disclosed in this application.

The composition of this additional supplement is specifically adapted to make sure it is suitable for patients with PKU. Moreover, the levels of vitamins, minerals, trace elements, and long chain polyunsaturated fatty acids are adapted in such a way that the daily intended intakes of these nutrients can be achieved without exceeding tolerable upper limits.

TABLE 1 of example 1

| | Total amount (daily intake) | Standard supplement (per serving) | Invention formula (per serving) |
|---|---|---|---|
| Energy (kcal) | 447 | 118.6 | 90.8 |
| Protein/Protein Equivalent (g) | 60 | 20 | — |
| Carbohydrates (g) | 43 | 8.8 | 16.5 |
| Fat (g) | 3.89 | 0.38 | 2.76 |
| Of which DHA (22:6n-3; mg) | 1.2 | 0.16 | 0.71 |
| Micronutrients* | | | |
| Calcium (mg) | 1068 | 356 | — |
| Phosphorus (mg) | 828 | 276 | — |
| Vitamin E (mg α-TE) | 40 | 3.2 | 30.4 |
| Vitamin C (mg) | 80 | 17.8 | 26.6 |
| Folic acid (µg) | 400 | 120 | 40 |

TABLE 1-continued of example 1

| | Total amount (daily intake) | Standard supplement (per serving) | Invention formula (per serving) |
|---|---|---|---|
| Niacin/Vitamin B3 (mg) | 21.3 | 7.1 | — |
| Vitamin B6 (mg) | 1.74 | 0.58 | — |
| Vitamin B12 (µg) | 5.4 | 1.80 | — |
| Choline (mg) | 459 | 153 | — |
| Nucleotides | | | |
| Uridine-5'-monophosphate (mg) | 625 | — | 625 |
| Amino acids (g)** | | | |
| only essential aa | 34.07 | 11.36 | — |

*All other vitamins, minerals and trace elements are added at levels that are sufficient to cover daily requirements.
**Other amino acids are present to provide the total of 20 g PE per serving.

Example 2

3 servings per day; 2 standard supplements+1 serving of a novel formula

Daily nutritional requirements are provided by 2 servings of a standard amino acids- and micronutrients-containing supplement+1 serving containing the daily required amounts of the nutrients disclosed in this application as well as the same amounts of amino acids, vitamins, minerals, and trace elements as the other 2 supplements.

This additional supplement is specifically adapted to make sure it is suitable for patients with PKU. Moreover, the levels of vitamins, minerals, trace elements, and long chain polyunsaturated fatty acids are adapted in such a way that the daily intended intakes of these nutrients can be achieved without exceeding tolerable upper limits.

TABLE 2 of example 2

| | Total amount (daily intake) | Standard supplement (per serving) | invention formula (per serving) |
|---|---|---|---|
| Energy (kcal) | 410.7 | 118.6 | 173.5 |
| Protein/Protein Equivalent (g) | 60 | 20 | 20 |
| Carbohydrates (g) | 34.1 | 8.8 | 16.5 |
| Fat (g) | 3.81 | 0.38 | 3.05 |
| Of which DHA (22:6n-3; mg) | 1.2 | 0.16 | 0.88 |
| Micronutrients* | | | |
| Calcium (mg) | 1068 | 356 | 356 |
| Phosphorus (mg) | 828 | 276 | 276 |
| Vitamin E (mg α-TE) | 40 | 3.2 | 33.6 |
| Vitamin C (mg) | 80 | 17.8 | 44.4 |
| Folic acid (µg) | 400 | 120 | 160 |
| Niacin/Vitamin B3 (mg) | 21.3 | 7.1 | 7.1 |
| Vitamin B6 (mg) | 1.74 | 0.58 | 0.58 |
| Vitamin B12 (µg) | 5.4 | 1.80 | 1.8 |
| Choline (mg) | 459 | 153 | 153 |
| Nucleotides | | | |
| Uridine-5'-monophosphate (mg) | 625 | — | 625 |
| Amino acids (g)** | | | |
| only essential aa | 34.07 | 11.36 | 11.36 |

*All other vitamins, minerals and trace elements are added at levels that are sufficient to cover daily requirements.

Example 3

3 servings per day; 3 servings of a novel formula

Daily nutritional requirements are provided by 3 servings of an amino acids- and micronutrients-containing supplement that also contain the daily required amounts of nutrients disclosed in this application.

Each serving provides ⅓ of the intended daily intakes of vitamins, minerals, trace elements and long chain polyunsaturated fatty acids, as well as ⅓ of the daily amount of the nutrients disclosed in this application. The formula is specifically adapted to patients with PKU.

TABLE 3 of example 3

| | Total amount (daily intake) | invention formula (per serving) |
|---|---|---|
| Energy (kcal) | 472.3 | 157.4 |
| Protein/Protein Equivalent (g) | 60 | 20 |
| Carbohydrates (g) | 49.5 | 16.5 |
| Fat (g) | 3.81 | 1.27 |
| Of which DHA (22:6n-3; mg) | 1.2 | 0.4 |
| Micronutrients* | | |
| Calcium (mg) | 1068 | 356 |
| Phosphorus (mg) | 828 | 276 |
| Vitamin E (mg α-TE) | 40 | 13.33 |
| Vitamin C (mg) | 80 | 26.67 |
| Folic acid (µg) | 400 | 133.33 |
| Niacin/Vitamin B3 (mg) | 21.30 | 7.1 |
| Vitamin B6 (mg) | 1.74 | 0.58 |
| Vitamin B12 (µg) | 5.4 | 1.8 |
| Choline (mg) | 459 | 153 |
| Nucleotides | | |
| Uridine-5'-monophosphate (mg) | 625 | 208.33 |
| Amino acids (g) | | |
| only essential aa | 34.1 | 11.4 |

*All other vitamins, minerals and trace elements are added at levels that are sufficient to cover daily requirements.

Example 4 positive effect of the nutritional composition according to the invention on behavioural cognitive function and synaptic plasticity in the brain.

Material and Methods

Animals & Diets Used in the Experiment (FC)

FC is the active supplement that was added to three different Phe levels in a basal animal chow. The supplement was composed of is a specific combination of nutrients including uridine-5'-monophosphate, choline, and the n-3 polyunsaturated fatty acids (PUFAs) docosahexaenoic acid (DHA) and eicosapentaenoic acid.

In this experiment, the C57Bl/6 Pahenu2 mouse model was used. Male and female homozygeous (PKU) mice and wild-type (WT) littermates were obtained from our own breeding. Male and female mice were housed in separate rooms under the same 12:12 light/dark cycle, temperature and humidity conditions. 60 PKU individuals and 10 WT mice were subdivided into seven experimental groups, receiving different diets. The basal formula for all diets was AIN93G (Research Diet Services, Wijk bij Duurstede). The WT individuals received normal chow with a Phe content of 8.8 g/kg. The six groups of PKU mice arisen when the supplementation of FC and three different Phe contents was randomized.

This resulted in the following groups: The first two groups received the same AIN93G normal chow as previously described for WT individuals (Phe content of 8.8 g/kg). One of these groups received the diet without FC, the other group received the diet but with FC: indicated as Phe8.8 and Phe8.8+FC, respectively. The last groups received a low-Phe diet. This diet contained 4.0 g/kg Phe with or without FC: indicated Phe4.0 and Phe4.0+FC, respectively. Finally, a mid-Phe content group was created wherein the Phe levels sets were set in between the high-Phe and Low Phe groups. The content of the mid-Phe diet was 6.4 g/kg: indicated Phe6.4 and Phe6.4+FC, respectively. The levels of amino acids within the food are depicted in table 1. All diets met the minimal nutritional requirement for laboratory animals. The animals had ad libitum access to these diets and water for 12 weeks.

At the start of the experiment (post-natal day (PND) 28), the animals were weaned and a blood sample was taken by tail vein puncture. On PND 31, the animals were exposed to a circular open field arena and subsequently put on the different diets for 12 weeks. All animals were weighed daily between 16:00-18:00 in the first week of the experiment (PND 31-PND 38) and from then on weekly. Food intake was measured daily. Within these 12 weeks, blood collection was performed on PND 59 and 87. On PND 115, all animals were subjected to the same open field arena and were subsequently euthanized via a heart puncture to collect blood, followed by perfusion. All proceedings concerning animals within this study were approved by the ethical committee of the University of Groningen, The Netherlands.

and the pelleted DNA was air dried for at least 30 min. To prepare the DNA for qPCR, the pelleted DNA was resuspended in 200 µl TE-buffer (10 mM Tris-HCl; 1 mM EDTA), vortexed, and incubated for 10 min. at 55° C. Subsequently, the samples were centrifuged for 10 min at 15.000 relative centrifugal force (rcf), 50 times diluted with mineralized water, vortexed and again centrifuged for 10 min at 15.000 rcf.

A 96-wells plate (Biorad, HSP-9601) was loaded with 2 µl of the samples together with 5 µL of Mastermix. This mastermix contained:
TE-Buffer
PCR-mix (Bioline SensiMix™ Probe Kit (500 reactions))
  WT/PAH-enu2 forward CCG TCC TGT TGC TGG CTT AC
WT/PAH-enu2 reverse CAG GTG TGT ACA TGG GCT TAG ATC WT probe CCG AGT CZZ LCA LTG CA
PAH-enu2 probe CCG AGT CZL LCA CTG CA The primers were based on Genbank and replicated according to guidelines of Eurogentec. The WT probe was tagged with a FAM fluorphore and the PKU probe was tagged with a Yakima Yellow fluorophore (Epoch Biosciences). The plate was run in an ABI Prism 7500 sequence detection system. The cycle parameters were 95° C. for 10 min, 95° C. for 0.15 min and 60° C. for 1 min. This cycle was repeated 39 times.

Behavioural Measurements

On PND 31 and 115, all animals were subjected to an open field. In this behavioural paradigm, the animals were allowed to explore a circular open field (r=40 cm) with a

TABLE 1

Amino acid levels in the different nutritional compositions of the treatment groups Phe 8.8, Phe 6.4 and Phe 4.0.

| mg/kg | Phe8.8 WT | Phe8.8 − FC | Phe8.8 + FC | Phe6.4 − FC | Phe6.4 + FC | Phe4.0 − FC | Phe4.0 + FC | Minimal requirement |
|---|---|---|---|---|---|---|---|---|
| Alanine | 4106 | 4350 | 4833 | 4294 | 4126 | 4114 | 4044 | n.a. |
| Arginine | 5177 | 5060 | 4875 | 4902 | 4584 | 4839 | 4679 | 3000 |
| Aspartic acid | 12261 | 12003 | 11989 | 11564 | 10903 | 11046 | 11320 | n.a. |
| Cystine | | | | | | | | n.a. |
| Glutamic acid | | | | | | | | n.a. |
| Glycine | 2786 | 3298 | 3112 | 3119 | 2933 | 2806 | 2874 | n.a. |
| Histidine | 3478 | 3336 | 3066 | 3026 | 2699 | 3053 | 3033 | 2000 |
| Isoleucine | 7293 | 7023 | 7201 | 7294 | 7149 | 7139 | 7133 | 4000 |
| Leucine | 14170 | 14057 | 13952 | 13974 | 13926 | 14130 | 14161 | 7000 |
| Lysine | 10707 | 10690 | 9727 | 10509 | 8946 | 9818 | 9925 | 4000 |
| Methionine | 4403 | 4196 | 4226 | 4211 | 3845 | 4155 | 4061 | 5000 |
| Phenylalanine | 7623 | 7567 | 7392 | 5420 | 5218 | 3388 | 3377 | 7600 |
| Proline | | | | | | | | n.a. |
| Serine | 8465 | 8079 | 8350 | 8595 | 8231 | 8470 | 8601 | n.a. |
| Threonine | 6005 | 5698 | 5553 | 5895 | 5523 | 5457 | 5719 | 4000 |
| Tryptophan | 1526 | 1567 | 1525 | 1554 | 1508 | 1558 | 1553 | 1000 |
| Tyrosine | 8659 | 8467 | 8601 | 8515 | 8373 | 8633 | 8393 | n.a. |
| Valine | 8555 | 8421 | 8422 | 8612 | 8274 | 8398 | 8193 | 5000 |

Genotyping

To establish genotype of the animals, quantitative PCR (qPCR) analysis was performed on DNA extracted from tail tissue. The DNA isolation procedure was initiated by incubating tail tissue in 0.5 mL mouse tail lysis buffer (100 mM Tris-HCl, pH 8.5; 5 mM EDTA, pH 8.0; 200 mM NaCl; 0.2% (w/v) SDS) and proteinase K (100 µg/ml, ratio 100:1) overnight at 55° C. at 600 rounds/minute (rpm). The next day the samples were vortexed and centrifuged for 10 min at 13.000 rpm. Subsequently, 450 µL of the supernatant was transferred into a new tube containing 0.5 mL isopropanol. After gently mixing of these solutions, the tube was centrifuged for 10 min at 6000 rpm. The supernatant was removed white surface and grey sides. Several minutes before the start of every trail, the arena was cleaned with 30% ethanol. At the beginning of a trail, the animal was placed in the centre of the arena in which he could freely explore the arena for 10 minutes. Each trail was recorded and tracked with the EthoVision system (Noldus, the Netherlands). The following behaviours were obtained from this system: Time, frequency and latency to the first enter centre zone, middle zone and border zone, distance moved, velocity, and number of zone transitions.

Figure 1A:
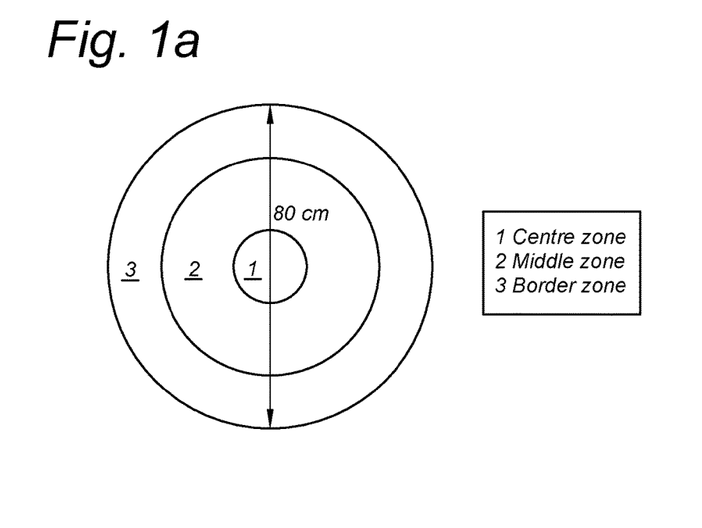
FIG. 1A shows the definition of the different zones; an open field of 80 cm was used. The analysis program distinguished between three zones: centre, middle and border.
Figure 1B:
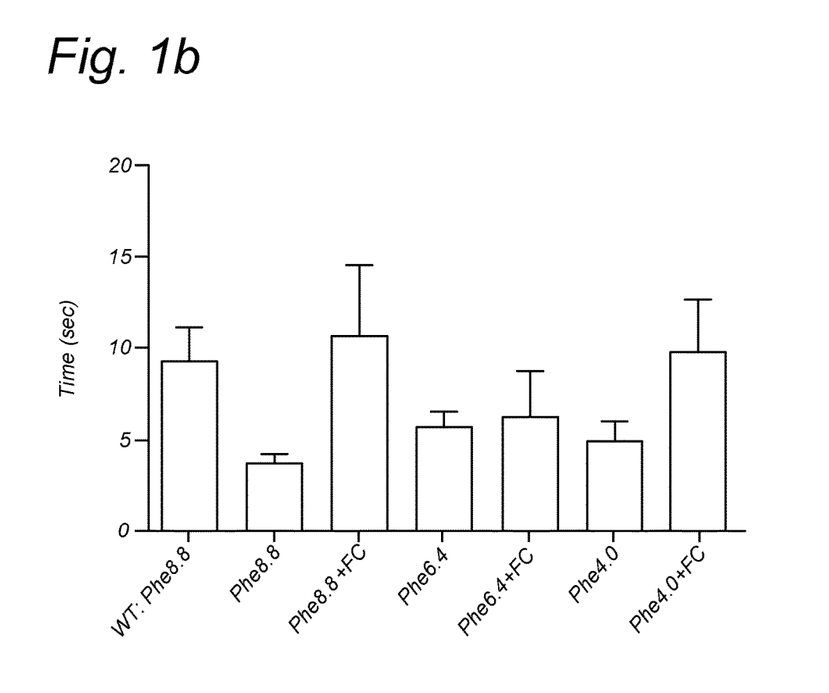
In FIG. 1B the time to leave the entre zone is presented for the different intervention and control groups.

The results are plotted in FIG. 1. FIG. 1A shows the definition of the different zones; an open field of 80 cm was used. The analysis program distinguished between three zones: centre, middle and border. In FIG. 1B the time to leave the centre zone is presented for the different intervention and control groups.

Immunohistochemistry

For immunohistochemistry, brains of the animals were collected through perfusion with paraformaldehyde (PFA). Immediately after heart punction, the animal was prepared in such a way that the heart was visible. The needle, connected to a pump system, was inserted into the left ventricle. Subsequently, the right atrium was cut and the rinsing solution (0.9% NaCl; 5 mL heparine/L) was passed through at a speed of 9.25 rpm equivalent to 15 ml/min. When the liver became pale, the rinsing solution was changed to fixation solution (4% PFA in 0.1M phosphate buffer (PB); pH7.4). After perfusion, the brain was collected and post-fixated for 24 hrs in fixation solution. After 24 hours, the brains were stored in 0.1M phosphate-buffered saline (PBS) at 4° C. In batches, the brains were put in a sucrose solution (30% sucrose 0.01M PB). This solution was used to act as a cryoprotectant. The brains were frozen with liquid nitrogen immediate after they descended to the bottom of the container (approximately 16 hours after submersion of brains into sucrose solution) and stored at −80° C. The brains were cut in two batches on the Leica CM3050 cryostate. The slices were cut on 20 μM and the chamber and object temperature was kept between −16° C. and −14° C. Slices were stored in 0.01M PBS with 0.1% sodium azide (NaN3) at 4° C.

Immunochemistry staining of PSD-95 was performed as follows: free-floating sections (5 hippocampus, 5 prefrontal and 5 striatum slices) were 3 times rinsed with 0.01 M Tris-buffered saline, pH7.4 (TBS) before incubation with 0.3% H2O2 in TBS. Sections are rinsed again 4 times with TBS and incubated with 1:1000 monoclonal mouse Anti-PSD-95, Millipore, MABN68, 1% NGS and 0.5% Triton-X in TBS for 2 hours in water bath at 37° C. Following incubation at 37° C., the sections were left on room temperature on the shaker for 24 hours and subsequently stored for 48 hours at 4° C. The sections are rinsed 6 times with TBS, before incubation of secondary antibody solution (1:500 Biotin-SP-conjugated affiniPure Goat-anti-Mouse, Jackson, code: 115-0.65-166 Lot#110630, 1% NGS and 0.5% Triton-X in TBS) for 2 hours on room temperature. The sections were rinsed 4 times with TBS, stored at 4° C. overnight and rinsed again 2 times before incubation with 1:400 AB complex, Vectastain PK-6100 standard in TBS for 2 hours. After incubation the slices were rinsed 6 times with TBS and placed on a 3,3'-diaminobenzidine (DAB; 7 mg/15 mL) solution. Color development was initiated by introduction of 100 μL 0.1% H2O2 in H2O to the DAB solution. The reaction was stopped trough rinsing 3 times with TBS. The sections were stored overnight at 4° C. before mounting with gelatin solution (1% Gelatin; 0.05% Aluin in H2O). Slides with the mounted slices were run through a series of 7 baths (2.3-100% Alcohol, 4-70% Alcohol 30% Xylol, 5-30% Alcohol 70% Xylol, 6,7,8-100% Xylol) before coverslipping with DPX. Slides were air dried at least 7 days before analysis.

For quantification, the Quantimet 550 image analysis system (Leica, Cambridge, UK) was used. A macro was designed to measure at a 10 times magnification the corrected optical density from a hand drawn region. The following regions were measured: Stratum Oriens, CA1 pyramidal cells, Stratum radiatum, two sub-regions of the molecular layer (Mol. layer (IV) Mol. layer (V) on the dorsal side of the dentate gyms and Mol. layer (IX) and Mol. layer (X) on the ventral side of the dentate gyms), the inner blade and the outer blade of the dentate gyms, the hilus, Stratum lucidum and the granular cells of the CA3. The optical density of these regions was corrected for the optical density of the corpus callosum.

Statistical Analysis

Body weight and food intake were measured weekly. For both data sets, the repeated measures ANOVA with a Bonferroni post-hoc test were used.

Several parameters in the open field were not normally distributed. Therefore, the Kruskal-Wallis test was used to examine differences in distance moved, velocity and time spend in the different zones. The data obtained from the transition between zones and latency to leave the centre zone was normally distributed. Therefore, t-tests were used to examine the differences between WT and PKU on PND 31 and PND 115. A One-way ANOVA was used to examine the differences between all groups in the latter parameter.

Finally, the PSD-95 immunohistochemical data was not normally distributed. Therefore, the Kruskal-Wallis test was used to examine if there were differences between the groups. The Dunn's Multiple Comparison Test was used to unravel which groups differed significantly from each other.

Indistinct Phenotype of C57Bl/6 PKU Mouse in the Round Open Field

The open field paradigm was used to examine differences in spontaneous behavior between WT and the PKU on the different diets. To establish a phenotype of the PKU mice, the following parameters were compared between the WT and PKU individuals on PND 31 and WT and PKU individuals on high Phe without FC on PND 115: Time, frequency and latency to the first enter centre zone, middle zone and border zone, distance moved, velocity and zone transitions. Male and female were grouped together while no significant differences are found in any parameter for gender. No significant differences were found for velocity, distance moved and time spent in the different zones on PND 31. There were differences found in zone transition in which PKU individuals show less zone transitions from centre to middle zone and from middle to border zone (Centre to middle zone: T-test (t=2,759 df=68) p=0.007, Middle to Border zone T-test (t=2.140 df=68) p=0.036).

A significant difference was found between the WT and PKU individuals on high Phe without FC group in latency to leave the centre zone (T-test (t=2,709 df=12) p=0.019).

Nutritional Treatment Restores PSD-95 Reduction in Proximal Hippocampal Synapses in PKU Individuals on High-Phe Diet.

To investigate the effect of FC on synapse formation and plasticity of excitatory synapses, PSD-95 was used as a post-synaptic marker. The corrected optical density was calculated for 12 subareas of the hippocampus. These 12 areas could be roughly subdivided into proximal and distal synapses. The proximal synapse areas included: CA3, inner and outer blade of the dentate gyms and the CA3. The distal synapse areas included: Stratum Oriens, Stratum radiatum, the molecular layer subdivided in Mol. layer (IV), Mol. layer (V), Mol. layer (IX) and Mol. layer (X), hilus and Stratum lucidum. Non-parametric testing revealed a significant difference between the diets in corrected optical density in the inner and outer blade of the dentate gyms (Inner blade; p=0.041, Outer blade p=0.024). The Dunn's Multiple Comparison Test showed a significant difference between the WT: Phe8.8 and the PKU on the same diet (p<0.05). This result could explain the positive effect of the nutritional treatment on the behavior of the Phe8.8 group.

Conclusion

The observed phenotype of PKU mice in high Phe-group was restored to WT level when the composition according to the invention (FC) was supplemented in the same Phe content group (FIG. 1). FC increases PSD-95 expression in hippocampal proximal synapses in the High-Phe group, indicating the neuronal synapse function was improved in the PKU mice. These findings suggest that FC has a beneficial effect on the proximal synapses of the dentate gyrns, an area which receives excitatory input from the entorhinal cortex. The hippocampus but also the entorhinal cortex are areas which are involved in learning and memory. A beneficial effect of FC in this area indicates a beneficial effect in learning and memory in this PKU model.

The invention claimed is:

1. A method for preserving and improving cognitive function and reducing cognitive deficit in phenylketonuria (PKU) or hyperphenylalaninemia patients, comprising administering to said patient in need thereof a nutritional composition comprising:
   a. a protein fraction consisting of free amino acids and at least 50 wt % glycomacropeptide, wherein the protein fraction has less than 1.0 wt % of phenylalanine,
   b. one or more of uridine and cytidine, or salts, phosphates, acyl derivatives or esters thereof;
   c. docosahexaenoic acid (22:6; DHA) and eicosapentaenoic acid (20:5; EPA), or esters thereof; and
   d. choline,
   such that, per day,
   (i) 0.08-3 g of the cumulative amount of the one or more of uridine and cytidine, or salts, phosphates, acyl derivatives or esters thereof,
   (ii) 400-5000 mg per day of the sum of DHA and EPA and esters thereof; and
   (iii) more than 50 mg of choline, is administered.

2. The method according to claim 1, wherein the protein fraction comprises less than 0.1 wt % phenylalanine based on total protein content.

3. The method according to claim 1, wherein the nutritional composition is administered to provide 200-600 mg choline per daily dose.

4. The method according to claim 1, wherein the protein fraction comprises at least 50 wt % glycomacropeptide (GMP) based on the total protein content.

5. The method according to claim 1, wherein the nutritional composition is a liquid composition further comprising a combination of pectin and at least one indigestible carbohydrate selected from the group consisting of xanthan gum and guar gum.

6. The method according to claim 5, wherein the viscosity of the nutritional composition is between 5 and 1500 mPa s, at 20° C. and a shear rate of 100/s.

7. A nutritional composition, comprising:
   (a) a protein fraction consisting of free amino acids and at least 50 wt % glycomacropeptide, wherein the protein fraction has less than 1.0 wt % of phenylalanine,
   (b) a fat fraction comprising 1-40 wt. % docosahexaenoic acid (22:6; DHA) or esters thereof, based on total fatty acids; and 0.5-20 wt. % eicosapentaenoic acid (20:5; EPA) or esters thereof, based on total fatty acids,
   (c) 50 to 3000 mg choline per 100 ml of the composition,
   (d) 0.08-3 g of the total sum of one or more of uridine and cytidine, or salts, phosphates, acyl derivatives or esters thereof per 100 ml of the composition, and
   (e) optionally, a carbohydrate fraction comprising between 5-70 en % digestible and optionally between 1-5 en % indigestible carbohydrates, based on the total energy content of the composition.

8. The nutritional composition according to claim 7, wherein the nutritional composition comprises between 30-65 en % protein, and between 1 and 15 en % fat, and between 1 and 60 en % digestible carbohydrates based on the total energy content of the composition, and wherein the composition is a liquid with a total caloric density between 50 and 300 kcal/100 ml.

9. The nutritional composition according to claim 7, wherein choline is present in an amount of 200-1000 mg per 100 ml.

10. A method for dietary management of PKU or hyperphenylalaninemia patients, comprising administering a supplement comprising (a) one or more of uridine and cytidine, or salts, phosphates, acyl derivatives or esters thereof;
   (b) docosahexaenoic acid (22:6; DHA) and eicosapentaenoic acid (20:5; EPA); and (c) choline, in conjunction with a nutritional composition comprising a protein source substantially devoid of phenylalanine, wherein the total daily intake of both the supplement and the nutritional composition is between 40-80 g protein, between 25-45 g carbohydrates, 0.08-3 g per day of the cumulative amount of the one or more of uridine and cytidine, or salts, phosphates, acyl derivatives or esters thereof, 400-5000 mg per day of the sum of DHA and EPA and esters thereof; and (c) more than 50 mg per day of choline.

11. A method for preserving and improving cognitive function and reducing cognitive deficit in phenylketonuria or hyperphenylalaninemia patients or preserving and improving cognitive function and reducing cognitive deficit associated with phenylketonuria or hyperphenylalaninemia, comprising administering to said patient in need thereof the nutritional composition according to claim 7.

12. A method for preserving and improving cognitive function and reducing cognitive deficit in phenylketonuria or hyperphenylalaninemia patients, comprising administering to said patient in need thereof a supplement comprising (a) one or more of uridine and cytidine, or salts, phosphates, acyl derivatives or esters thereof; (b) docosahexaenoic acid (22:6; DHA) and eicosapentaenoic acid (20:5; EPA); and (c) choline, wherein said supplement is administered in conjunction with a nutritional composition comprising a protein source substantially devoid of phenylalanine, wherein the total daily intake of both the supplement and the nutritional composition is between 40-80 g protein, between 25-45 g carbohydrates, 0.08-3 g per day of the cumulative amount of the one or more of uridine and cytidine, or salts, phosphates, acyl derivatives or esters thereof, 400-5000 mg per day of the sum of DHA and EPA and esters thereof; and (c) more than 50 mg per day of choline.

13. The method according to claim 12, comprising administering choline in an amount of 200-1000 mg per 100 ml per day.

14. A method for treatment or providing nutritional management of hyperphenylalaninemia patients or phenylketonuria patients, said method comprising administering to said patients a composition comprising:
  a. a protein fraction consisting of free amino acids and at least 50 wt % glycomacropeptide, wherein the protein fraction has less than 1.0 wt % of phenylalanine,
  b. one or more of uridine and cytidine, or salts, phosphates, acyl derivatives or esters thereof;
  c. docosahexaenoic acid (22:6; DHA) and eicosapentaenoic acid (20:5; EPA), or esters thereof, and
  d. choline, and
  optionally a carbohydrate fraction comprising between 5-70 en % digestible carbohydrates based on the total energy content of the composition,
  such that, per day,
  (i) 0.08-3 g of the cumulative amount of the one or more of uridine and cytidine, or salts, phosphates, acyl derivatives or esters thereof,
  (ii) 400-5000 mg per day of the sum of DHA and EPA and esters thereof; and
  (iii) more than 50 mg of choline, is administered.

15. A method for treatment of hyperphenylalaninemia patients or phenylketonuria patients, said method comprising administering said patients a composition supplement comprising (a) one or more of uridine and cytidine, or salts, phosphates, acyl derivatives or esters thereof; (b) docosahexaenoic acid (22:6; DHA) and eicosapentaenoic acid (20:5; EPA); and (c) choline, wherein said supplement is administered in conjunction with a nutritional composition comprising a protein source substantially devoid of phenylalanine, wherein the total daily intake of both the supplement and the nutritional composition is between 40-80 g protein, between 25-45 g carbohydrates, 0.08-3 g per day of the cumulative amount of the one or more of uridine and cytidine, or salts, phosphates, acyl derivatives or esters thereof, 400-5000 mg per day of the sum of DHA and EPA and esters thereof, and (c) more than 50 mg per day of choline.

16. The nutritional composition according to claim 6, wherein the nutritional composition comprises uridine in an amount of 100-2000 mg per 100 ml.

17. The method according to claim 12, wherein the nutritional composition comprises uridine in an amount of 100-2000 mg per 100 ml.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: artificial
<220> FEATURE:
<223> OTHER INFORMATION: primer

<400> SEQUENCE: 1
ccgtcctgtt gctggcttac                                              20

<210> SEQ ID NO 2
<211> LENGTH: 24
<212> TYPE: DNA
<213> ORGANISM: artificial
<220> FEATURE:
<223> OTHER INFORMATION: primer

<400> SEQUENCE: 2
caggtgtgta catgggctta gatc                                         24
```